United States Patent
Machado et al.

(10) Patent No.: US 7,074,962 B2
(45) Date of Patent: Jul. 11, 2006

(54) CATALYST HOLDER AND AGITATION SYSTEM FOR CONVERTING STIRRED TANK REACTOR TO FIXED BED REACTOR

(75) Inventors: Reinaldo Mario Machado, Allentown, PA (US); James Edward Koniski, Souderton, PA (US); Stephen Kohler, Slatington, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 558 days.

(21) Appl. No.: 10/076,813

(22) Filed: Feb. 15, 2002

(65) Prior Publication Data

US 2003/0157003 A1    Aug. 21, 2003

(51) Int. Cl.
*C07C 209/00*    (2006.01)
(52) U.S. Cl. ...................... 564/397; 564/305
(58) Field of Classification Search ............... 564/305, 564/441, 307; 422/211, 214, 221, 222, 224, 422/225, 227, 228, 234
See application file for complete search history.

(56) References Cited

U.S. PATENT DOCUMENTS

| 4,743,577 | A |   | 5/1988 | Schroeder et al. ............ 502/326 |
| 5,779,995 | A | * | 7/1998 | Witt et al. .................... 422/215 |
| 6,086,832 | A | * | 7/2000 | Ohta ............................ 422/211 |
| 2002/0081254 | A1 | * | 6/2002 | Boger ........................... 422/222 |

FOREIGN PATENT DOCUMENTS

| DE | 101 04 849 A 1 | 7/2001 |
| WO |      9830323   | 7/1998 |

OTHER PUBLICATIONS

Hatziantoniou, et al., "Mass Transfer and Selectivity in Liquid-Phase Hydrogenation of Nitro Compounds in a Monolithic Catalyst Reactor with Segmented Gas-Liquid Flow", Ind. Eng. Chem. Process Des. Dev., vol. 25, No. 4, 964-970 (1986).

Albertus J. Sandee, et al., "ROTACAT: A Rotating Device Containing a Designed Catalyst for Highly Selective Hydroformylation", Adv. Synth. Catal. 2001, 343, pp. 201-206.

* cited by examiner

*Primary Examiner*—Thurman Page
*Assistant Examiner*—Karl Puttlitz
(74) *Attorney, Agent, or Firm*—Keith D. Gourley

(57) ABSTRACT

This invention relates to apparatus particularly a monolith catalytic reactor in a stirred tank reactor. The stirred tank reactor including the fixed bed catalytic reactor apparatus comprises:

an housing having an open top and open bottom portion supportably maintained with said tank, said housing having a substantially outwardly extending, horizontal baffle near its top portion said baffle having a least one perforation in its surface, and said housing having at least one perforation in the wall near its top portion;

a fixed bed catalyst system supportably retained within said housing permitting both liquid and gas flow therethrough; and, an agitator shaft terminating in a turbine blade substantially adjacent the perforation in the wall of said housing, said agitator having a passageway including an opening in an upper portion thereof to the interior of an upper part of said tank and terminating in an opening adjacent the turbine blade.

6 Claims, 4 Drawing Sheets

CATALYST HOLDER AND AGITATION SYSTEM FOR CONVERTING STIRRED TANK REACTOR TO FIXED BED REACTOR

BACKGROUND OF THE INVENTION

Industrial two phase reactions, such as hydrogenation reactions, are often performed by using finely divided powdered slurry catalysts in stirred-tank reactors. These slurry phase reaction systems are inherently problematic in chemical process safety, operability and productivity. The finely divided, powdered catalysts are often pyrophoric and require extensive operator handling during reactor charging and filtration. By the nature of their heat cycles for start-up and shutdown, slurry systems promote co-product formation which can shorten catalyst life and lower yield to the desired product.

An option to the use of finely divided powder catalysts in stirred reactors is the use of fixed bed reactors, e.g., pelleted and particulate catalysts or monolith catalysts. While this reactor technology does eliminate much of the handling and waste problems associated with stirred tank reactors, there are a number of engineering challenges. E.g., inadequate mixing and inadequate heat transfer have not permitted the general application of fixed bed reactor technology to reactions involving many organic compounds. On the other hand, stirred tanks provide for excellent mixing assuring homogeneity of reactants and they provide for excellent heat transfer. It is highly desirable to attain the benefits of fixed bed catalysts and stirred tank reactors to be combined in a practical reactor system.

The following articles and patents are representative of catalytic processes employing monolith catalysts and processes in two-phase chemical reactions including the hydrogenation of nitroaromatics and other organic compounds.

Hatziantoniou, et al. in "Mass Transfer and Selectivity in Liquid-Phase Hydrogenation of Nitro Compounds in a Monolithic Catalyst Reactor with Segmented Gas-Liquid Flow", Ind. Eng. Chem. Process Des. Dev., Vol. 25, No. 4, 964–970 (1986) discloses the isothermal hydrogenation of nitrobenzene and m-nitrotoluene dissolved in ethanol using a monolithic catalyst impregnated with palladium. The authors report that the activity of the catalyst is high and therefore mass-transfer is rate determining. Hydrogenation was carried out at 590 and 980 kPa at temperatures of 73 and 103° C. Again, less than 10% conversion per pass was achieved. Ethanol was used as a co-solvent to maintain one homogeneous phase.

U.S. Pat. No. 4,743,577 discloses metallic catalysts which are extended as thin surface layers upon a porous, sintered metal substrate for use in hydrogenation and decarbonylation reactions. In forming a monolith, a first active catalytic material, such as palladium, is extended as a thin metallic layer upon a surface of a second metal present in the form of porous, sintered substrate. The resulting catalyst is used for hydrogenation, deoxygenation and other chemical reactions. The monolithic metal catalyst incorporates catalytic materials, such as, palladium, nickel and rhodium, as well as platinum, copper, ruthenium, cobalt and mixtures. Support metals include titanium, zirconium, tungsten, chromium, nickel and alloys.

WO 98/30323 discloses a process for carrying out a reaction between a reactant gas and reactant liquid in the presence of a monolith catalyst. In operation, a reactor is filled with reactant liquid and the monolith catalyst is rotated about a horizontal shaft, alternately in the liquid phase and then in the gas phase.

In an article entitled *ROTACAT: A Rotating Device Containing a Designed Catalyst for Highly Selective Hydroformylation*, Adv. Synth. Catal. 2001, 343, 201–206 there is disclosed a 200 mL autoclave which is charged with two parallel monolith cylindrical tubes which are rotated about a vertical axis. Reaction is effected while the monolith catalytic reactor is rotated within the liquid medium.

BRIEF SUMMARY OF THE INVENTION

This invention relates to an apparatus, i.e., a catalyst holder for converting a stirred tank reactor into a fixed bed catalytic reactor. The stirred tank reactor including the fixed bed catalytic reactor apparatus comprises:

a tank having an opening to permit access to the interior, a cover for sealing the opening, at least one inlet for introducing a liquid or a gaseous reactant or both and at least one outlet for removing product;

a housing having an open top and open bottom portion supportably maintained with said tank, said housing having at least one side perforation in the side wall near an upper portion thereof for permitting flow from the interior of the housing to said tank;

a substantially outwardly extending, horizontal baffle from an upper portion of said housing configured for effecting restrictive liquid flow between the interior wall of said tank and the edge of the baffle, said baffle having a least one perforation for permitting flow of liquid and gas therethrough;

a plurality of baffles extending from an upper portion of said housing and above said side perforation to at least the bottom portion of said housing, said baffles providing for restrictive liquid flow between the interior wall of said tank reactor and the baffles;

a fixed bed catalyst supportably retained within said housing permitting both liquid or gas flow or both therethrough; and, an agitator shaft having a turbine blade coupled thereto, said turbine blade positioned within said housing and substantially adjacent the at least one side perforation in the side wall of said housing. Preferably, when the reactor is used for gas phase reactions, the agitator has a passageway between an upper portion of the autoclave and a point substantially adjacent the turbine blade for providing for flow of gas from an upper portion or headspace of said autoclave to said point adjacent said turbine blade.

There are several advantages of this invention and they include:

an ability to retrofit stirred tank reactors and autoclaves thereby converting them from slurry phase catalytic reactors to fixed bed catalytic reactors;

an ability to eliminate reactor loops, pumps, etc. commonly used in fixed bed and monolith catalytic reactors, particularly those that employ external heat exchangers;

an ability to enhance the solubilization of the reactant gas in the reactant liquid for catalytic reaction;

an ability to maintain homogeneity of the reactants and reaction products;

an ability to enhance circulation rate and effect short mixing and blend times due to the high flow rate generated by the turbine impeller through a fixed bed catalytic reactor;

an ability to perform two phase reactions in an autoclave using a fixed bed catalyst, e.g., a monolith catalyst; and, an ability to overcome agitation problems where the fixed bed catalytic reactor is affixed to the agitation mechanism and rotated.

DETAILED DESCRIPTION OF THE INVENTION

This invention relates to an improved apparatus and method for carrying out fixed bed catalytic reactions in a stirred tank reactor, e.g., an autoclave equipped with agitation continuously or batch.

Two phase reactions using a fixed bed catalytic reactor present some difficult problems. One difficulty is that of obtaining substantially uniform dispersion or mixing of gas and liquid for reaction. Sometimes, when effecting these reactions, particularly in a monolith catalytic reactor, gas or liquid is introduced within a single channel but the mixture is not. As a result, side reactions often occur causing byproduct buildup and possibly, dangerous conditions. Poor conversion is another aspect of improper mixing. Single phase reactions are more easily carried out in fixed bed reactors but heat transfer, circulation rate and heat transfer can be limited. Then, too, single phase reactions, such as, liquid/liquid may employ slurry phase catalysts which present catalyst recovery problems.

In the present invention, a catalyst holder and agitation system is introduced to a stirred tank or autoclave and it is used to effect the catalytic reaction. To facilitate an understanding of the invention reference is made to the drawings.

Figure 1:
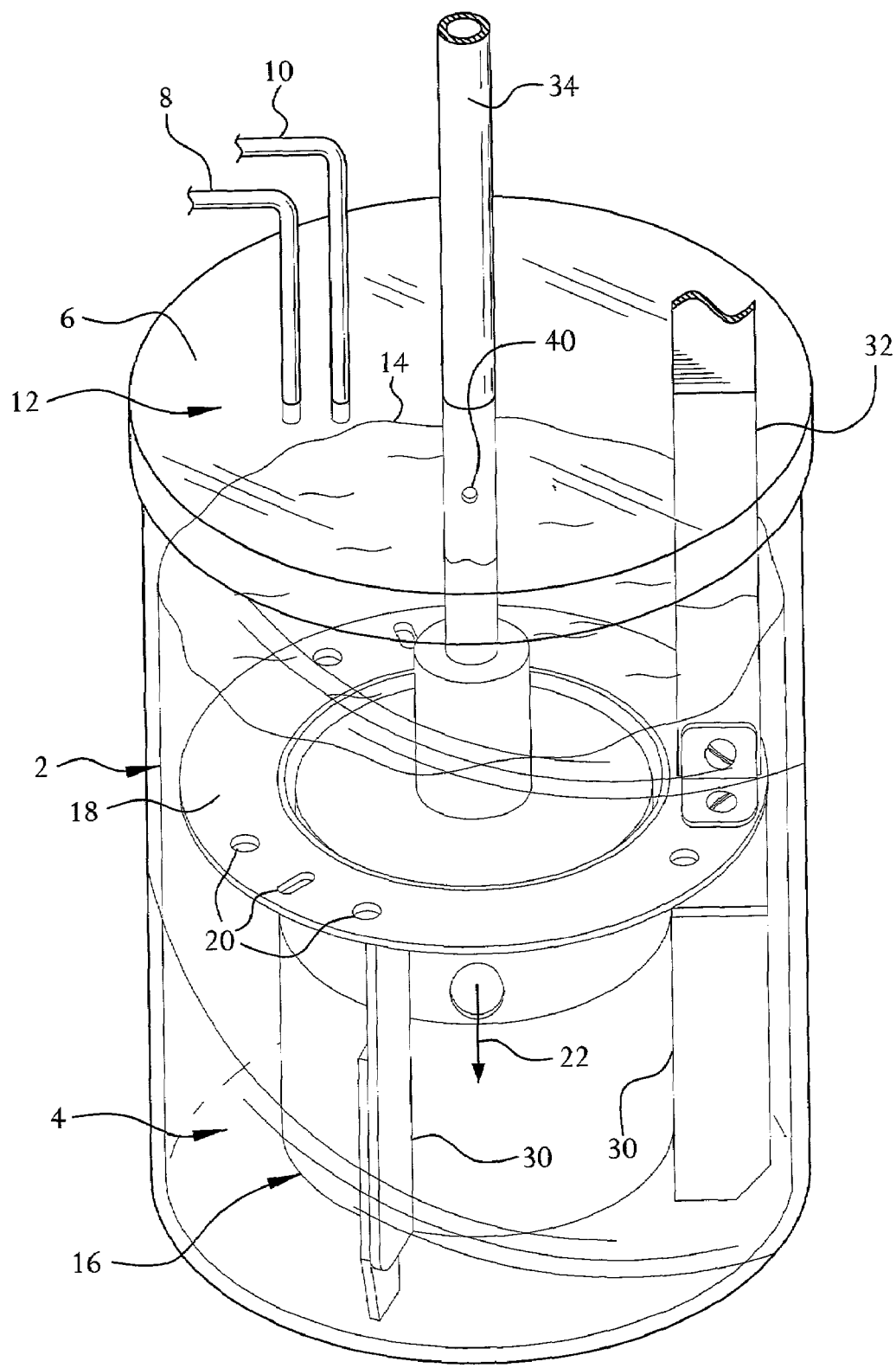
FIG. 1 is an isometric view of said autoclave including said fixed bed catalyst holder and a fixed bed catalyst.
Figure 2:
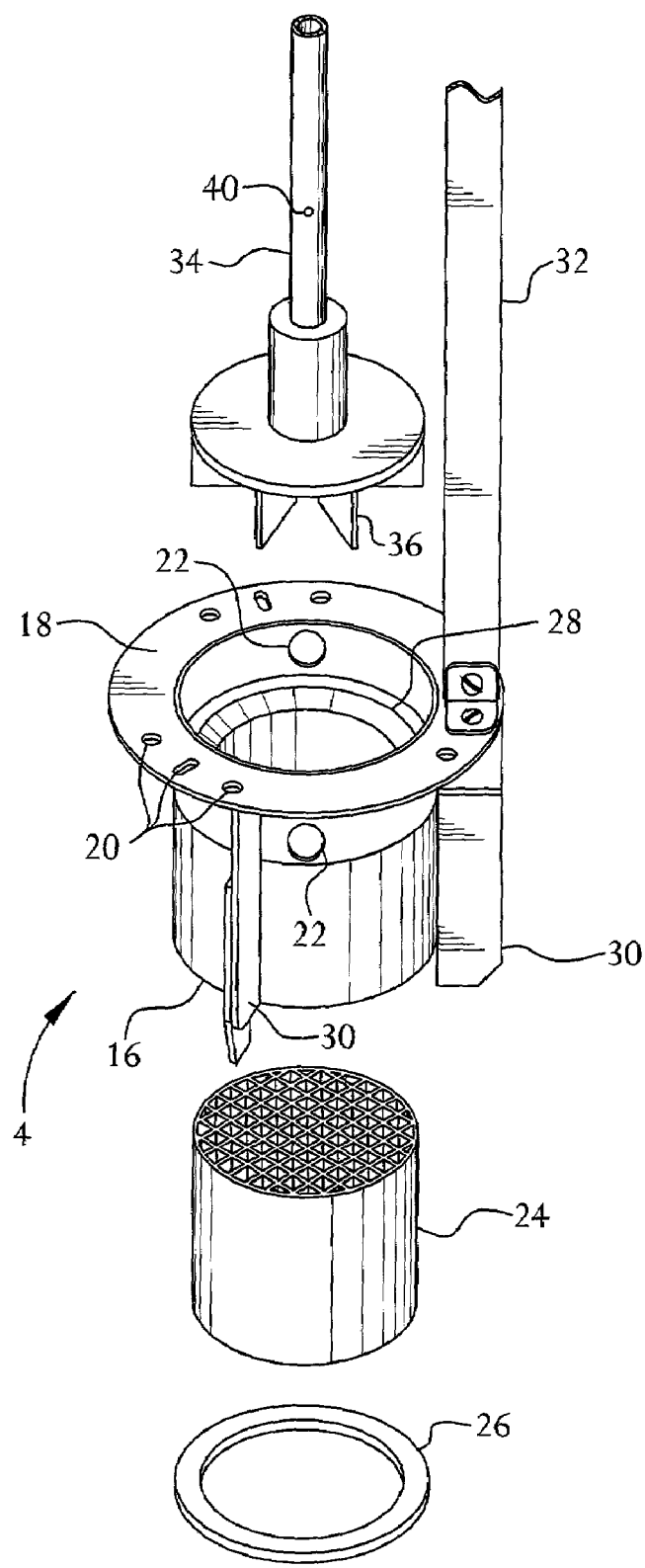
FIG. 2 is an assembly view of the fixed bed catalyst holder including the fixed bed catalyst and agitation system.
Figure 3:
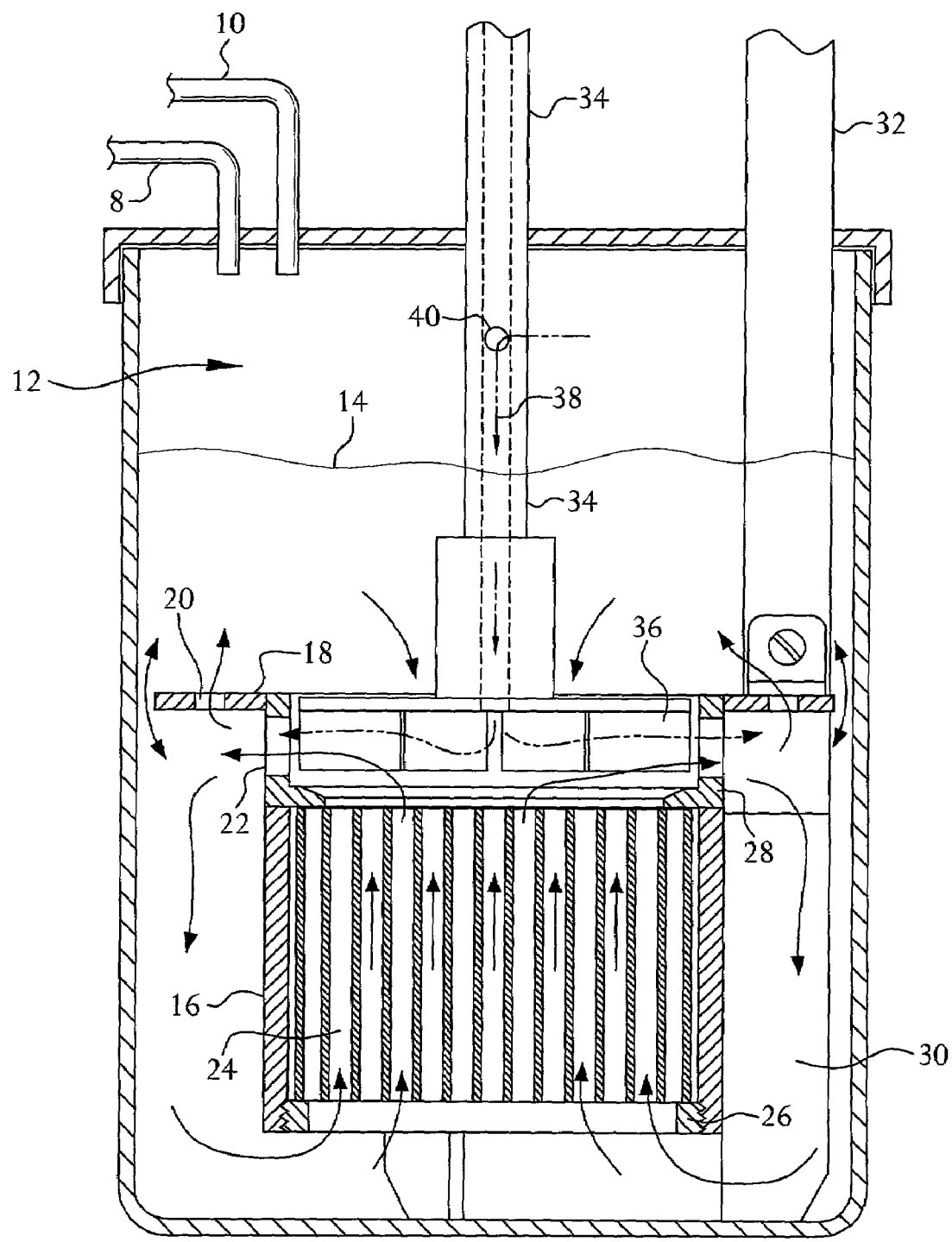
FIG. 3 is a view in cross-section of the autoclave including the fixed bed catalyst holder illustrated in FIG. 1.

FIGS. 1–3 describe an autoclave 2 which is of conventional configuration including a fixed bed catalyst holder 4. The autoclave 2 has an opening typically at the top to gain access to the interior and a cover 6 for closing the opening. Inlet and exit lines 8 and 10 are provided to introduce reactants to autoclave 2 and to remove product. The inlet and exit lines 8 and 10 can be one in the same, but it is preferred they are separate. There may be more than one inlet and one exit line and the number is at the discretion of the designer of the autoclave. Often there is a sampling line (not shown) that provides access for taking samples and monitoring the reaction. The autoclave typically is cylindrical in configuration but other variations are possible. Heat exchangers (not shown) either internal (coils) or external (jacketed) to the autoclave are commonly provided to maintain the temperature of the reactor contents. Sufficient reactive liquid(s) then is provided in the autoclave to fully submerge the fixed bed catalyst holder 4 and, yet, leave room for the collection of gas in headspace 12 above liquid level 14.

The fixed bed catalyst holder 4 is comprised of a housing 16 that is open at its top and its bottom. A horizontal baffle 18 is positioned at an upper point on the housing and configured to the contour of the interior wall of the autoclave in order to restrict liquid flow between the edge of the horizontal baffle 18 and the interior wall of the autoclave 2. (Note the space between the edge of horizontal baffle 18 and the interior wall of autoclave 2 as shown by the arrows in FIG. 3). At least one, and preferably a plurality of perforations 20, is present in horizontal baffle 18 to permit upward flow of liquid and gas (as shown by the arrows) therethrough. Often, a plurality of perforations 20 is provided uniformly about the periphery of horizontal baffle 18.

The housing 16 has at least one side wall perforation 22, preferably a plurality of perforations 22 uniformly distributed about the circumference of housing 16, extending through the side wall of the housing 16 at a point below the horizontal baffle 18 but above the outlet of a fixed bed catalyst 24 to be described. The sidewall perforation 22 permits flow of liquid and gas from the interior of the housing 16 to a point exterior of the housing 16 and within the autoclave 2 as shown by the arrow.

A fixed bed catalyst 24, e.g., a monolith catalyst is placed within housing 16 in a way such that reactant liquid(s) and reactant gas can pass from the bottom of the housing 16 through the fixed bed catalyst 24 and out the side wall perforations 22 in the upper end of housing 16. Often there is a plurality of perforations 22 distributed uniformly about the periphery of housing 16. The fixed bed catalyst 24 is supported by threaded sealing ring 26 that engages the bottom portion of housing 16. To prevent upward movement of the fixed bed catalyst in the housing 16, a retaining ring 28 is provided. In the situation where the fixed bed catalyst 24 is based upon particulate material, pellets, etc., a screen or grid may be placed at the top and bottom portions to retain the particulate fixed bed catalyst in place.

Side baffles 30 are placed external to housing 16 and are used to direct gas and liquid in an axial and downward flow direction and generally opposite the direction of gas and liquid flow in the fixed bed catalyst 28. If desired, side baffles 30 are vertically positioned and extend below the bottom of housing 16 for supporting and maintaining housing 16 from sealing engagement with the bottom of autoclave 2. (Other means than side baffles 30 may be used to provide support for housing 16.) It is necessary to maintain a space between the bottom of the housing 16 to permit flow of liquid and gas there between. The use of the side baffles 30 thus not only provides for support but for effecting liquid and gas flow direction. Side baffling may also be positioned on the interior walls of the autoclave and are deemed equivalent to those positioned on housing 16 but it is preferred to have baffling affixed to the housing 16.

To prevent rotation and other movement of fixed bed catalyst holder 4 within the autoclave 2 a support arm 32 is provided so that attachment (not shown) may be made to the autoclave itself. Other means than support arm 32 may be used to maintain the fixed bed catalyst holder 4 in a fixed location.

The housing 16 is designed such that minimal gas and liquid can pass between the outer edge of the fixed bed catalyst 24, e.g., a monolith catalyst and the interior wall of housing 16. In that way a substantial portion of the reactant liquid(s), reactant gas and product is forced through the fixed bed catalyst.

The last piece of equipment necessary to effect catalytic reaction is the inclusion of an agitation system that includes motor (not shown) coupled to agitator shaft 34 at one end and a turbine blade 36 coupled to the agitator shaft 34 at the other end. Disc or vane turbine impellers are commonly used as turbine blades. To effect gas/liquid reactions, agitator shaft 34 has an axial passageway 38 that is positioned for discharge of gas at or near turbine blade 36 at one end and inlet 40 at another point in headspace 12 of autoclave 2. Preferably the axial passageway 38 is internal to agitator shaft 34 but it can also be a tube, etc. external thereto. The axial passageway 38 thus provides for a flow of reactant gas from the headspace 12 to the turbine blade 36.

The agitation system provides the driving force necessary for catalytic reaction. In operation, turbine blade 36, typically a disc or vane impeller, which is positioned proximate and adjacent side wall perforations 22 in housing 16 forces liquid and gas radially and outwardly through side wall perforations 22. This action causes liquid reactant above horizontal baffle 18 to be drawn into the upper opening of housing 16. Reactant gas also is drawn from the headspace 12 through the axial passageway 38 in shaft 34 and discharged at a point adjacent turbine 34. Gas inlet 40 allows introduction of gas from the headspace 12 to passageway 38. Impingement of reactant liquid and reactant gas with the turbine blade 36 generates a frothy and intimate mixture of finely divided gas bubbles and reactant liquid. Thus, an upper flow pattern is established by the agitation system.

The agitation system also creates a second flow pattern. The frothy mixture of reactant gas and reactant liquid after exiting housing 16 through side wall perforations 22, is directed downwardly within autoclave 2 and external to housing 16. The frothy mixture passes beneath the housing 16 and into the interior. Then, the mixture is passed upwardly through the fixed bed catalyst 24. This flow pattern is established by virtue of horizontal baffle 18 and side baffles 30. Too much space between the wall of autoclave 2 and horizontal baffle 18 and the wall and side baffle 30 may detract from the desired downward flow of reactants. The flow pattern can also be disrupted by not including side baffles. Without side baffles the frothy mixture tends to swirl and avoid passing through the fixed bed catalyst 24. When there is a desired flow pattern of reactant liquid(s) and reactant gas, the reactants pass through the fixed bed catalyst 24 and contacted with the active component from inlet to outlet.

There are numerous categories of gas/liquid and gas/liquid/liquid reactions where the liquids are immiscible. Such reaction can be carried out in the retrofitted autoclave. One class of reaction is the hydrogenation of organic compounds, which includes hydrogenation of a mixture of immiscible liquids. Commonly used solvents in slurry phase and fixed bed catalytic reactions may be used in the process if the presence of immiscible liquids cause problems. Examples of commonly used solvents include lower alkanols, e.g., methanol, ethanol and propanol, iso or normal; tetrahydrofuran and glycols, e.g., ethylene glycol and diethylene glycol. The amount of solvent used in hydrogenation reactions for example typically ranges from 1 to about 50% by weight of the charge.

The following are representative organic compounds that can be hydrogenated in a monolith catalytic reactor retrofitted into a stirred tank autoclave.

Nitro Group Reduction

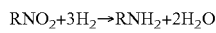

where R is aromatic. Nitro aromatics are capable of undergoing the hydrogenation reaction described by the process of this invention. Typical nitroaromatics are nitrobenzene, nitrotoluenes, nitroxylenes, nitroanisoles and halogenated nitroaromatics where the halogen is Cl, Br, I, or F.

Olefins are another group and these include straight chain, cyclic and aromatics. Examples include toluene, benzene and nitro, carboxyl, hydroxyl and amine derivatives thereof such as aniline, toluidine, toluenediamine, mononitrotoluene, nitrobenzoic acid and so forth.

Anhydride Reduction to Lactone or Ether

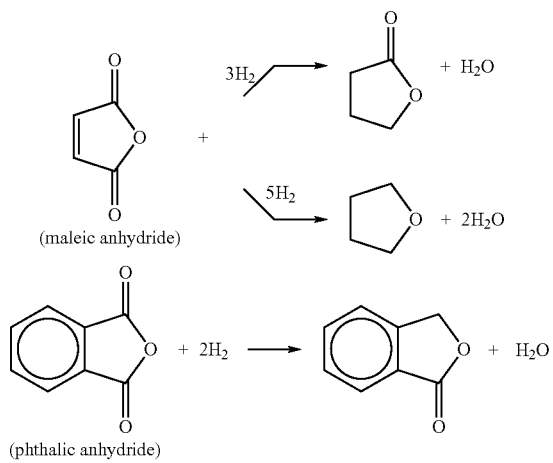

Anhydrides such as maleic anhydride and phthalic anhydride are first hydrogenated to γ-butyrolactone and phthalide respectively. The γ-butyrolactone can be further reduced to tetrahydrofuran.

Reductive Alkylation or Reductive Amination

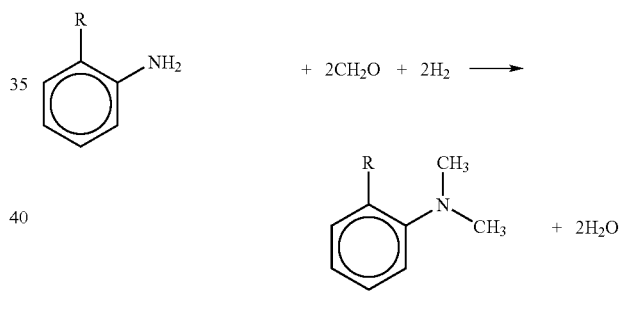

R'CHO+NH$_3$+H$_2$→R'CH$_2$NH$_2$+H$_2$O

When an aldehyde or a ketone is treated with ammonia or a primary or secondary amine in the presence of hydrogen and a hydrogenation catalyst, reductive alkylation of ammonia or the amine or reductive amination of the carbonyl compound takes place. R and R' can be aromatic or aliphatic. Examples of aldehydes and ketones useful in the hydrogenation reactions include formaldehyde, cyclohexanone and methyl isopropyl ketone. Reaction products resulting from the reaction of these aldehydes and ketones with primary and secondary amines include N-methylcyclohexylamine, N-methyldicyclohexylamine, N,N-dimethylcyclohexylamine, N-ethylcyclohexylamine, dicyclohexylamine, N,N-diethylcyclohexylamine, N,N,N'-trimethylaminoethylethanolamine, N-ethyl-1,2-dimethylpropylamine and N,N,N',N'-tetramethylpropanediamine.

One class of fixed bed catalytic reactor suited for effecting a retrofit of the stirred tank, slurry phase reactor is a monolith catalytic reactor. These reactors broadly are classified as continuous solid phase and continuous void phase from an inlet to an outlet. Typically the monolith catalysts consist of an inorganic porous substrate, a metallic substrate, or a modified substrate having a plurality of channels coated with a catalytic metal. The modification can be an inorganic coating derived from a carbon or a heat treated network polymer. Often the monolith catalytic reactors are based upon long narrow capillary channels, circular, square, rectangular or other geometric shape, whereby gas and liquid are co-currently passed through the channels under a laminar flow regime. These channels are present within arrange of from 100 to 1500, preferably from 400 to 800 channels per square inch.

Other types of fixed bed catalyst may also be used. Examples include pellets, spheres, as well as coated substrates, e.g., rings and saddles, wire mesh, etc. The metal catalytic component also may be incorporated onto particulate supports. Examples of supports include alumina, silica, kieselguhr, clays, diatomaceous earth, zeolites, e.g., X, Y, A and ZSM; carbon, and polymeric. Catalytic metals may also be deposited on or impregnated into particulate supports or they may be particulate in themselves. Screens or other systems conventionally employed for retaining the particulate catalyst components in the catalyst holder may be used.

Catalytic metals suited for incorporation into the monolith catalytic reactor or onto supports, for effecting reactions such as hydrogenation include: Group VIb, Group VIIb, Group VIII, and Group Ib metals of the periodic table. Examples of catalytic metal components include cobalt, nickel, Raney or sponge nickel, palladium, platinum, copper, rhodium, ruthenium, rhenium and so forth. Often a mixture of metals are employed, one example being palladium and nickel. Catalytic metals are impregnated into the monolith substrate via a washcoat. The washcoat composition comprised of catalytic metals is typically identified as a weight percent within the washcoat itself. The washcoat may be applied in an amount of from 1 to 50% of the monolith total weight. Typical catalyst metal loadings, then, range from 0.1 to 25% by weight and preferably from 1 to 10% by weight of the washcoat. The catalytic metals may be incorporated into the monolith substrate or support in a manner generally recognized by the art. Incipient wetness from a salt solution of the catalytic metal is one example of a method for incorporating a metal catalytic component on the monolith substrate or modified monolith substrate.

The fixed bed catalyst is sized that it has a catalyst volume typically from about 5 to 50 percent of the volume of the autoclave. This volume allows for excellent circulation rate through the catalyst bed, e.g., 0.1 seconds to about 5 seconds with a liquid velocity of from 0.01 to 1 meter/second. An overall gas hold-up of from 5 to 50% in the stirred tank reactor is preferred.

EXAMPLE 1

Hydrogenation of Nitrobenzene in a Stirred Tank Autoclave Converted to Fixed Bed Reactor In effecting a two-phase reaction such as the hydrogenation of nitrobenzene in a 2 liter Parr reactor fitted with the catalyst holder and agitation system.

Catalyst Pretreatment

A 2-inch long×2-inch diameter 5% Pd/carbon monolith catalyst having 400 channels per square inch was mounted in the fixed bed catalyst holder described in FIG. 1 providing an effective monolith catalyst diameter of 1.75 inches. This assembly was placed in the 2 L Parr reactor and sealed. After room temperature dry leak testing with nitrogen, then hydrogen, then depressurizing, one liter of 2-propanol was added to the reactor. The reactor was pressurized to 200 psig with hydrogen, heated over 30 minutes to 140° C. with stirring at 1000 rpm, maintained at 140° C. for 30 minutes, and then cooled to room temperature. The reactor was emptied.

Nitrobenzene Hydrogenation

To the above Parr reactor including the monolith catalyst was added one liter of 40 wt % nitrobenzene in 2-propanol (364.7 g nitrobenzene plus 548.3 g of 2-propanol) to provide a liquid level above the horizontal baffle. The Parr reactor was sealed, pressurized with hydrogen to 35 psig and heated to 140° C. over 30 minutes. The pressure was increased with hydrogen to 200 psig with stirring maintained at 1000 rpm.

The action of the turbine impeller creates a low pressure zone at the point of agitation. That action causes hydrogen to be drawn from the headspace through the passageway in the agitator shaft and dispensed adjacent the turbine. Also, reactor liquid above the horizontal baffle is drawn to the turbine impeller. Rotation of the turbine causes the hydrogen to break into finely divided bubbles and cause dissolution of hydrogen in the liquid nitrobenzene phase. In doing so, a frothy mixture is created. Because of the restriction of liquid flow upward into an upper part of the autoclave by the horizontal baffle, a major portion of the frothy mixture is forced downwardly to the bottom of housing. The resultant reaction mixture then passes to the inlet of the monolith catalyst, then upwardly through the monolith catalyst to the outlet. The reaction product comprised of aniline, unreacted nitrobenzene and hydrogen are removed at the outlet of the monolith catalyst. The process is repeated with the reaction mixture and incoming reactant from above the horizontal baffle being discharged through the side wall perforation in the housing.

A portion of the frothy mixture exiting the side wall perforations in the housing is allowed to pass to an upper portion of the autoclave by virtue of the perforations in the horizontal baffle. Unreacted hydrogen is vented to the headspace and liquid flows to an upper portion of the housing.

Hydrogen uptake is monitored using a ballast and hydrogenation is complete after 40 minutes at 140° C. minutes in the Parr reactor. The hydrogen uptake throughout the reaction was between 50 and 75 moles $H_2/m^3$ of catalyst/sec. At that point, the reaction was terminated and the product removed from the Parr reactor.

Figure 4:
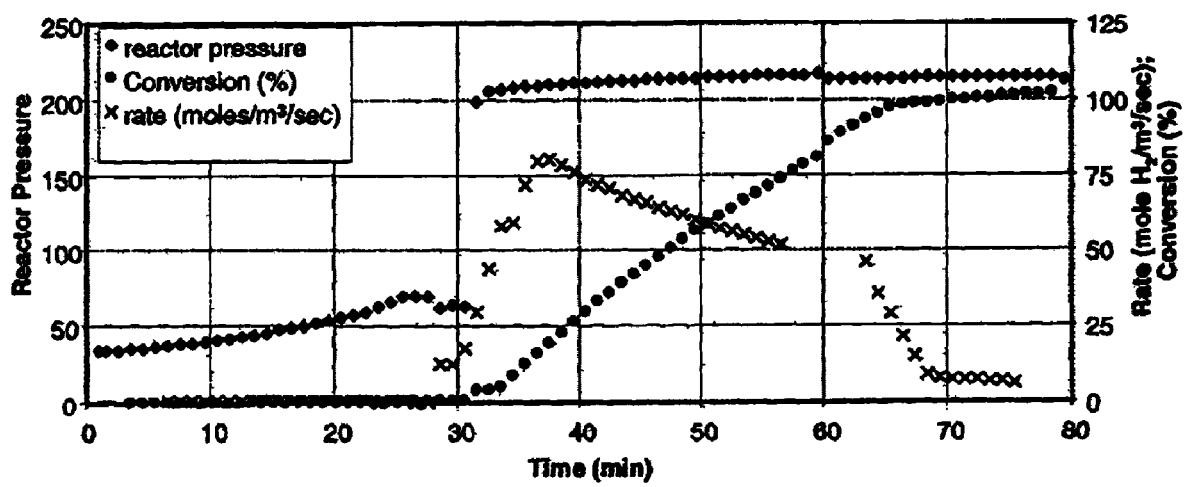
FIG. 4 is a graph of reaction criteria as a function of time.

By gas chromatographic analysis, nitrobenzene conversion was 99.9%. Aniline selectivity was roughly 95%. The graph on FIG. 4 shows the reaction criteria as a function of time.

What is claimed is:

1. In a process for carrying out a reaction between a reactant gas and reactant liquid in a stirred tank having at least a portion of reactant gas residing in a headspace portion of an autoclave, the improvement which comprises:
    (a) inserting a fixed bed catalyst holder in said tank comprised of a housing having an open top and open bottom portion supportably maintained with said tank, said housing having a substantially outwardly extending, horizontal baffle near its top portion and adapted for substantial sealing engagement with the interior wall of said tank, said baffle having a least one perforation in its surface, and said housing having at least one side wall perforation in the wall near its upper portion permitting flow from the interior of the housing to said tank;
    (b) supportably retaining a fixed bed catalyst within said housing permitting both liquid and reactant gas flow therethrough;

(c) extending an agitator shaft into said tank and terminating in a turbine blade substantially adjacent the side wall perforation in the wall of said housing, said agitator having a gas passageway including an opening in the headspace portion of said autoclave and terminating in an opening adjacent the turbine blade;

(d) effecting agitation at a point adjacent the side wall perforation in the wall of said housing causing liquid and reactant gas to be passed from the interior of the housing through the perforations to the interior of the autoclave;

(e) drawing reactant gas hydrogen from the headspace in said autoclave through a passageway in said agitator to a point adjacent the turbine;

(f) forcing a mixture of reactant liquid and reactant gas via baffling from a point adjacent the side wall perforations in said housing to the inlet of the fixed bed catalyst by means of baffles extending from the top to at least the bottom portion of said housing; and then, (g) reacting the mixture of reactant gas and reactant liquid.

2. The process of claim 1 wherein the reaction is a hydrogenation reaction.

3. The process of claim 2 wherein the reactant liquid is a nitroaromatic compound.

4. The process of claim 3 wherein the nitroaromatic compound is dinitrotoluene.

5. The process of claim 3 wherein the nitroaromatic compound is nitrobenzene.

6. The process of claim 3 wherein the fixed bed catalyst within said housing is a monolith catalytic reactor comprising a monolith substrate and a catalytic metal.

* * * * *